US010779733B2

(12) United States Patent
Pratt et al.

(10) Patent No.: US 10,779,733 B2
(45) Date of Patent: Sep. 22, 2020

(54) TELEMEDICINE APPLICATION OF VIDEO ANALYSIS AND MOTION AUGMENTATION

(71) Applicant: AT&T INTELLECTUAL PROPERTY I, L.P., Atlanta, GA (US)

(72) Inventors: James H. Pratt, Round Rock, TX (US); James E. Jackson, Austin, TX (US); Eric Zavesky, Austin, TX (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 1248 days.

(21) Appl. No.: 14/885,746

(22) Filed: Oct. 16, 2015

(65) Prior Publication Data

US 2017/0105621 A1 Apr. 20, 2017

(51) Int. Cl.
*A61B 5/00* (2006.01)
*A61B 5/11* (2006.01)
(Continued)

(52) U.S. Cl.
CPC .......... *A61B 5/0077* (2013.01); *A61B 5/1113* (2013.01); *A61B 5/1114* (2013.01);
(Continued)

(58) Field of Classification Search
CPC ... G06F 19/3418; A61B 5/0022; A61B 5/411; A61B 5/117
See application file for complete search history.

(56) References Cited

U.S. PATENT DOCUMENTS 5,441,047 A  8/1995 David et al.
5,701,904 A  12/1997 Simmons et al.
(Continued)

FOREIGN PATENT DOCUMENTS

WO  9904043  1/1999
WO  9927842  6/1999
WO  2009095021  8/2009

OTHER PUBLICATIONS

Starkington, "Proactive Passive Monitoring Sensors Debut, Define New Telehealth Category," Home Health News, homehealthnews. org, Jun. 21, 2010. http://www.homehealthnews.org/2010/06/proactive-passive-monitoring-sensors-debut-define-new-telehealth-category/.
(Continued)

*Primary Examiner* — Jeffrey G Hoekstra
*Assistant Examiner* — Jason M Ip
(74) *Attorney, Agent, or Firm* — Amin, Turocy & Watson, LLP

(57) ABSTRACT

A system for providing video analysis and motion augmentation, particularly in the context of telemedicine applications is disclosed. In particular, the system may utilize cameras and other devices to detect macro and micro changes and movements of a being so as to assist in the detection of an anomaly associated with the being. After detecting the anomaly based on the detected macro and micro changes and movements, the system may transmit an alert identifying the anomaly and formulate a proposed request for interaction with the being. The request for interaction may be transmitted to the being, and information obtained in response to the request for interaction may be utilized by the system to assist in the determination of a diagnosis of a condition of the being. The process may be repeated as necessary until the diagnosis is confirmed and enough information associated with the being is obtained.

20 Claims, 3 Drawing Sheets

(51) Int. Cl.
*G16H 50/20* (2018.01)
*G16H 80/00* (2018.01)
*G16H 30/40* (2018.01)

(52) U.S. Cl.
CPC ........... *A61B 5/7275* (2013.01); *G16H 30/40* (2018.01); *G16H 50/20* (2018.01); *G16H 80/00* (2018.01); *A61B 5/0022* (2013.01); *A61B 5/747* (2013.01)

(56) References Cited

U.S. PATENT DOCUMENTS

| | | | |
|---|---|---|---|
| 6,610,010 | B2 | 8/2003 | Sjöqvist |
| 6,697,103 | B1 | 2/2004 | Fernandez et al. |
| 6,816,603 | B2 | 11/2004 | David et al. |
| 9,092,556 | B2 | 7/2015 | Amble et al. |
| 9,098,611 | B2 | 8/2015 | Pinter et al. |
| 9,471,751 | B1* | 10/2016 | Kahn ................. G06F 16/335 |
| 2004/0054760 | A1 | 3/2004 | Ewing et al. |
| 2005/0149364 | A1 | 7/2005 | Ombrellaro |
| 2006/0036134 | A1 | 2/2006 | Tarassenko et al. |
| 2009/0112070 | A1 | 4/2009 | Lin et al. |
| 2010/0279718 | A1 | 11/2010 | Borve |
| 2011/0034209 | A1* | 2/2011 | Rubinsky .............. G06F 19/321 455/556.1 |
| 2011/0119661 | A1* | 5/2011 | Agrawal ............... G06F 21/566 717/154 |
| 2011/0267418 | A1 | 11/2011 | Galindo et al. |
| 2011/0301429 | A1 | 12/2011 | Henke |
| 2013/0018672 | A1 | 1/2013 | Wong et al. |
| 2013/0123667 | A1 | 5/2013 | Komatireddy et al. |
| 2013/0246097 | A1* | 9/2013 | Kenney ................. G06Q 50/24 705/3 |
| 2013/0322711 | A1* | 12/2013 | Schultz ............... G06F 19/3418 382/128 |
| 2014/0368687 | A1* | 12/2014 | Yu ...................... G06K 9/00604 348/222.1 |
| 2015/0065812 | A1 | 3/2015 | Pan |
| 2015/0110372 | A1 | 4/2015 | Solanki et al. |
| 2015/0120312 | A1 | 4/2015 | Hyde et al. |
| 2015/0193553 | A1* | 7/2015 | Petersen ............. G06F 16/9554 235/375 |

OTHER PUBLICATIONS

Rantz, "Using Sensor Technology to Augment Traditional Healthcare," 31st Annual International Conference of the IEEE EMBS, Sep. 2-6, 2009. http://medecon.pbworks.com/f/Rantz%20Sensor%20Technology.pdf.

Bifulco et al., "Telemedicine Supported by Augmented Reality: an interactive guide for untrained people in performing an ECG test," Biomedical Engineering Online 13.1 (2014): 153. http://www.biomedcentral.com/content/pdf/1475-925X-13-153.pdf.

* cited by examiner

TELEMEDICINE APPLICATION OF VIDEO ANALYSIS AND MOTION AUGMENTATION

FIELD OF THE INVENTION

The present application relates to technologies for video and motion augmentation, and more particularly, to a system and method for providing video analysis and motion augmentation, particularly in the context of telemedicine applications.

BACKGROUND

In today's society, medical professionals often rely on various types of devices to assist in the detection of various types of physical abnormalities and to assist in determining which disease or condition explains such abnormalities. Currently existing technologies for detecting anomalies often require the use of invasive medical tools or require non-portable and expensive devices to conduct various types of scans on patients. Invasive medical tools include devices, such as, but not limited to, endoscopes, catheters, probes, and surgical robots. As an example, physicians currently utilize endoscopes fitted with lens systems and eyepieces to examine a region inside a patient's body. In order to examine the patient's body, a physician typically inserts the endoscope directly into an opening or organ of the patient's body. While the endoscope itself is often useful in detecting abnormalities in the body of a patient, using an endoscope often causes patient discomfort and even physical trauma at the site at which the endoscope is inserted. Similarly, probes, catheters, surgical robots, and other invasive medical tools also can cause discomfort and physical trauma.

As an alternative to or in addition to using invasive tools, physicians may also utilize non-invasive diagnostic tools. Non-invasive diagnostic tools include devices, such as, but not limited to, X-ray machines, Magnetic Resonance Imaging (MRI) machines, computerized tomography (CT) machines, positron emission tomography (PET) machines, and other non-invasive diagnostic devices. As an example, physicians utilize MRI machines to generate magnetic fields and pulses of radio wave energy to generate pictures of organs and physical structures inside a patient's body. While MRI machines and other similar technologies produce helpful images and information to assist a physician in detecting anomalies and confirming medical diagnoses, such technologies are often very expensive, cumbersome, non-portable, or a combination thereof. As a result, there is still significant room to enhance current methodologies and technologies for detecting anomalies, obtaining patient information, and confirming medical diagnoses.

SUMMARY

A system and accompanying methods for providing video analysis and motion augmentation for applications, such as telemedicine applications, are disclosed. In particular, the system and methods may involve utilizing video analysis and motion augmentation to assist in the detection of various types of physical anomalies and to assist in the determination of diagnoses for beings, such as humans and animals. In order to accomplish the foregoing, the system and methods may involve utilizing cameras and other technologies to focus on two primary modalities associated with such beings: physiological changes and movements. Both of these modalities may be available at macro (e.g. body or body region) and micro (e.g. specific body structure or body part) levels. The system and methods may utilize the cameras and other technologies to capture video and/or other media content of a being in a particular environment, such as an office, home, or other environment. Based on the captured video and/or other media content of the being, the system and methods may include performing an analysis of the content to detect physiological changes and/or movements of the being at macro and micro levels. For example, based on the video of the being, the systems and methods may detect a micro-movement of a body part of the being or a change in skin pigmentation of the being.

Once the video or other content of the being is obtained and the detected changes of the being are detected, the system and methods may include submitting the content, the detected changes, and information associated with the content and changes for further processing in the system. The submitted content, changes, and information may be aggregated with similar information for other beings. Based on a comparison between the aggregated data, the content, the changes, and the information, the system and methods may detect one or more anomalies associated with the being. If an anomaly is not detected or a detected anomaly needs to be confirmed, the system and methods may include transmitting a signal to cause the cameras to be adjusted so that additional media content of the being may be obtained from a different vantage point and/or transmitting a signal to a device of the being to instruct the being to perform a particular action, such as move a body part in the presence of the camera. The cameras may obtain the additional media content based on the adjusted position of the camera and/or the action performed by the being in response to the instruction. Then, the system and methods may include utilizing the additional media content from the cameras in combination with the initial media content obtained of the user to confirm the existence of an anomaly.

Once an anomaly is detected, the system and methods may include transmitting one or more alerts to a device of the being or to a device of a physician monitoring the being, which indicate the presence and type of anomaly detected. The system and methods may also include generating and transmitting one or more proposed interactions to be performed with the being based on the detected anomaly. For example, if the cameras obtain video content of a person that shows that the person's left eye is twitching in an anomalous manner, the system may generate and transmit a proposed interaction that indicates that the person should blink their left eye in a certain manner and/or that the physician monitoring the person should perform some type of interaction with the person so as to obtain additional information. The system and methods may receive information back from the person and/or the physician that relates to the proposed interaction, and may utilize the information, in conjunction with the content, changes, aggregated data, and other information, to generate a diagnosis for the being. For example, using the example above, based on the media content showing the person's left eye twitching, information gathered after the person blinks their eye, aggregated information for other individuals experiencing similar symptoms, previously stored historical patient information for the person, and/or other information, the system and methods may diagnose the person with a certain eye disease. The system and methods may include continuing to monitor the being to confirm the diagnosis, to track the being's progress, to determine trends in a population, update the being's historical information, or to perform any other desired function. In certain embodiments, the content obtained from the cameras may be combined with other technologies, such as, but not limited to, infrared imaging content, thermal imaging content, MRI content, CT content, PET content, and/or any type of other content to confirm anomalies, confirm diagnoses, generate proposed interactions, transmit alerts, or any combination thereof.

In one embodiment, a system for providing video analysis and motion augmentation for telemedicine applications is disclosed. The system may include a memory that stores instructions and a processor that executes the instructions to perform various operations of the system. The system may perform an operation that includes capturing first media content of a being within a range of a camera monitoring the being. The system may then perform an operation that includes analyzing the first media content to detect a first change associated with the being. In certain embodiments, the first change associated with the being may be a movement of the being, a change in a condition of the being, or a combination thereof. The system may proceed to perform an operation that includes detecting an anomaly associated with the being based on comparing the first change associated with the being to aggregated data for a plurality of beings including the being. Once an anomaly is detected, the system may perform an operation that includes determining, based on the anomaly, a proposed interaction with the being. The system may perform an operation that includes transmitting the proposed interaction to a device of the being. Finally, the system may perform an operation that includes determining, based on the anomaly, the aggregated data, and on information obtained in response to transmitting the proposed interaction, a diagnosis associated with the being.

In another embodiment, a method for providing video analysis and motion augmentation for telemedicine applications is disclosed. The method may include utilizing a memory that stores instructions, and a processor that executes the instructions to perform the various functions of the method. In particular, the method may include obtaining, during a first time interval, first media content of a being within a range of a camera monitoring the being. Additionally, the method may include detecting, based on the first media content, a first change associated with the being. The first change associated with the being may include a movement of the being, a first change in a condition of the being, or a combination thereof. Once the first change is detected, the method may include detecting an anomaly associated with the being based on comparing the first change associated with the being to aggregated data for a plurality of beings. The method may then include determining, based on the anomaly associated with the being, a proposed interaction with the being, and then transmitting the proposed interaction to a device associated with the being. Finally, the method may include determining, based on the anomaly, the aggregated data, and on information obtained in response to transmitting the proposed interaction, a diagnosis associated with the being.

According to yet another embodiment, a computer-readable device having instructions for providing video analysis and motion augmentation for telemedicine applications is provided. The computer instructions, which when loaded and executed by a processor, may cause the processor to perform operations including: capturing first media content of a being within a range of a camera; analyzing the first media content to detect a first change associated with the being, wherein the first change associated with the being comprises a movement of the being, a first change in a condition of the being, or a combination thereof; detecting an anomaly associated with the being based on comparing the first change associated with the being to aggregated data for a plurality of beings; determining, based on the anomaly associated with the being, a proposed interaction with the being to determine a diagnosis associated with the being; transmitting the proposed interaction to a device associated with the being; and determining, based on the anomaly, the aggregated data, and on information obtained in response to transmitting the proposed interaction, the diagnosis associated with the being.

These and other features of the systems and methods for providing video analysis and motion augmentation for telemedicine applications are described in the following detailed description, drawings, and appended claims.

DETAILED DESCRIPTION OF THE INVENTION

Figure 1:
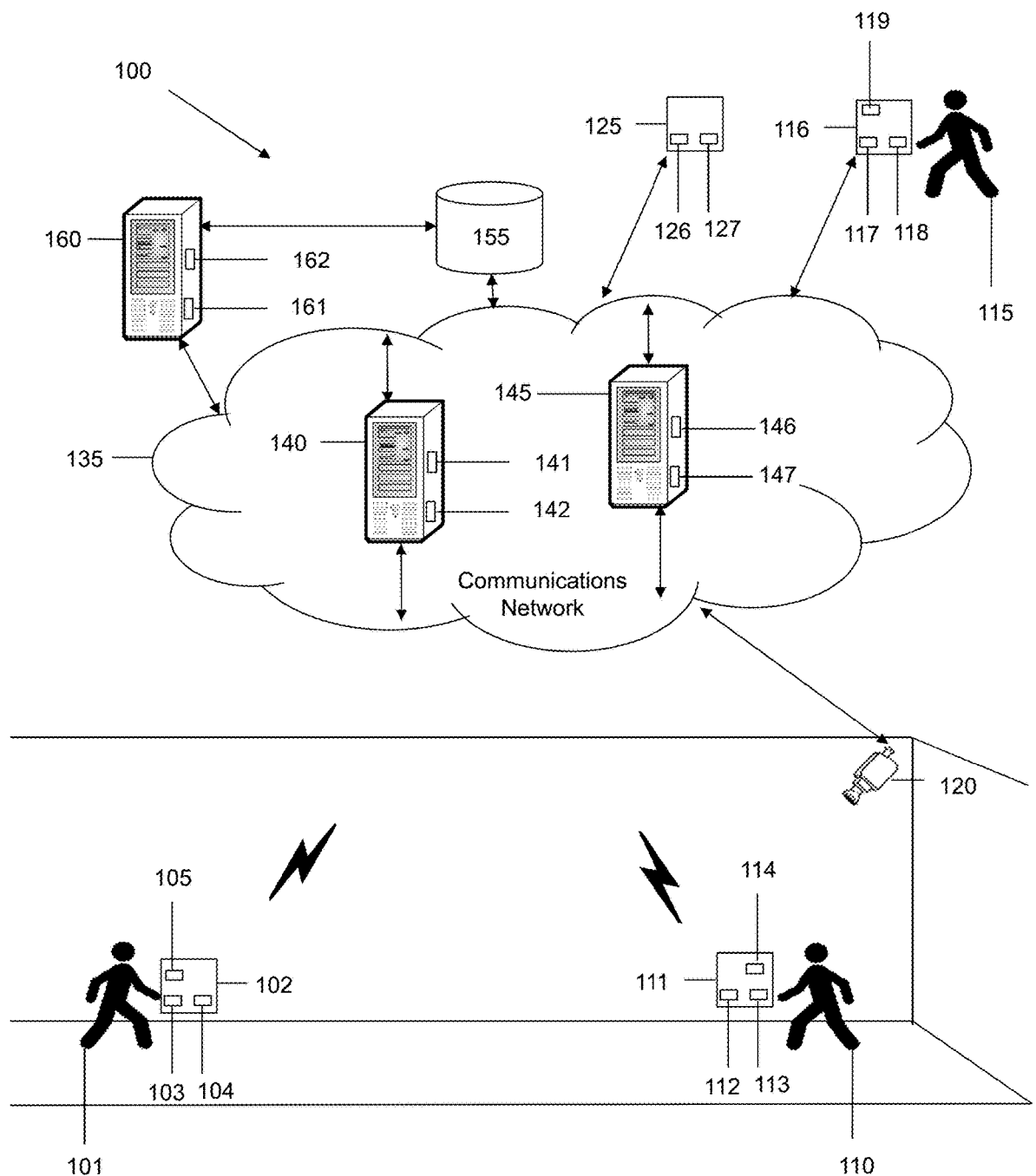
FIG. 1 is a schematic diagram of a system for providing video analysis and motion augmentation for telemedicine applications according to an embodiment of the present disclosure.

A system 100 and accompanying methods for providing video analysis and motion augmentation for applications, such as, but not limited to, telemedicine applications, are disclosed. In particular, the system 100 and methods may involve utilizing video analysis and motion augmentation to assist in the detection of various types of anomalies and to assist in the determination of diagnoses for various types of beings, such as humans and animals. In order to accomplish the foregoing, the system 100 and methods may involve utilizing cameras 120 and other technologies to focus on two primary modalities associated with such beings: physiological changes and movements. Each of these modalities may be available at macro (e.g. body or body region) and micro (e.g. specific body structure or body part) levels. The system 100 and methods may utilize the cameras 120 and other technologies to capture video and/or other media content of a being in a particular environment, such as a doctor's office, a home, or other environment. Based on the captured video and/or other media content of the being, the system 100 and methods may analyze the content to detect physiological changes and/or movements of the being at both macro and micro levels.

Once the video or other content of the being is obtained and the detected changes of the being are detected, the system 100 and methods may submit the content, the detected changes, and information associated with the content and changes for further processing in the system 100. The submitted content, changes, and information may be aggregated with similar information for other beings. Based on a comparison among the aggregated data, the content, the changes, and the information, the system 100 and methods may detect one or more anomalies associated with the being. If an anomaly is not detected or a detected anomaly needs to be confirmed, the system 100 and methods may include transmitting a signal to cause the cameras 120 to be adjusted so that additional media content of the being may be obtained from a different position. Additionally, the system 100 and methods may include transmitting a signal to a device of the being to instruct the being to perform a particular action, such as move a body part in front of the camera 120. The cameras 120 may obtain the additional media content based on the adjusted position of the camera 120 and/or the action performed by the being in response to the instruction sent to the being. The system 100 and methods may then include utilizing the additional media content from the cameras 120 in combination with the initial video content depicting the user to confirm the existence of an anomaly.

Once an anomaly is detected, the system 100 and methods may include transmitting one or more alerts to a device of the being and/or to a device of a physician monitoring the being. The alerts may be utilized to indicate the presence and type of anomaly detected. The system 100 and methods may also include generating and transmitting one or more proposed interactions to be performed with the being based on the detected anomaly. For example, if the cameras 120 obtain video content of a person that shows that his skin pigmentation on his right arm is changing, the system 100 may generate and transmit a proposed interaction that indicates that the person should rotate his arm in a certain manner and/or that the physician monitoring the person should perform some type of interaction with the person so as to obtain additional information relating to the anomaly.

The system 100 and methods may receive information back from the person and/or the physician that relates to the proposed interaction, and may utilize the information, in conjunction with the content, changes, aggregated data, and other information, to generate a diagnosis for the person. For example, using the example above, based on the media content showing the change in skin pigmentation, information gathered after the person rotates his arm, aggregated information for other individuals experiencing similar symptoms, previously stored historical patient information for the person, and/or other information, the system 100 and methods may diagnose the person with a certain skin disease. The system 100 and methods may include continuing to monitor the person to confirm the diagnosis, to track the person's progress, to determine trends in a population, update the person's historical information, or to perform any other desired function. In certain embodiments, the content obtained from the cameras 120 may be combined with information obtained from other technologies, such as, but not limited to, infrared imaging content, thermal imaging content, MRI content, CT content, PET content, and/or any other type of content to confirm anomalies, confirm diagnoses, generate proposed interactions, transmit alerts, or any combination thereof.

As shown in FIG. 1, a system 100 for providing video analysis and motion augmentation for applications, such as, but not limited to, telemedicine applications, is disclosed. The system 100 may be configured to support, but is not limited to supporting, cloud computing services, content delivery services, satellite services, telephone services, voice-over-internet protocol services (VoIP), software as a service (SaaS) applications, gaming applications and services, productivity applications and services, mobile applications and services, and any other computing applications and services. The system may include a first user 101, which may be any type of being, such, as but not limited to, a human, an animal, or any other being. The first user 101 may utilize a first user device 102 to access data, content, and services, or to perform a variety of other tasks and functions. As an example, the first user 101 may utilize first user device 102 to transmit signals to access various online services, such as those provided by a content provider or service provider associated with communications network 135. The first user device 102 may include a memory 103 that includes instructions, and a processor 104 that executes the instructions from the memory 103 to perform the various operations that are performed by the first user device 102. In certain embodiments, the processor 104 may be hardware, software, or a combination thereof. The first user device 102 may also include a camera 105, which may be configured to record and store video and/or audio content within a viewing range and/or auditory range of the camera 105. In certain embodiments, the camera 105 may be any type of camera including, but not limited to, a video camera, a photo camera, an infrared camera, a thermal imaging camera, any type of imaging device, or any combination thereof. In certain embodiments, the first user device 102 may be a computer, a medical device, a laptop, a tablet device, a phablet, a server, a mobile device, a smartphone, a smart watch, or any other type of computing device. Illustratively, the first user device 102 is shown as a smartphone device in FIG. 1, and the first user 101 is a person.

In addition to the first user 101, the system 100 may also include a second user 110, which may be any type of being, such, as but not limited to, a human, an animal, or any other being. The second user 110 may utilize a second user device 111 to also access data, content, and services, and to perform a variety of other functions. For example, the second user device 111 may be utilized by the second user 110 to transmit signals to request various types of content, services, and data provided by providers associated with communications network 135 or any other network in the system 100. The second user device 111 may include a memory 112 that includes instructions, and a processor 113 that executes the instructions from the memory 112 to perform the various operations that are performed by the second user device 111. In certain embodiments, the processor 113 may be hardware, software, or a combination thereof. The second user device 111 may also include a camera 114, which may be configured to record and store content within a viewing range of the camera 114. In certain embodiments, the camera 114 may be any type of camera including, but not limited to, a video camera, a photo camera, an infrared camera, a thermal imaging camera, any type of imaging device, or any combination thereof. Similar to the first user device 102, in certain embodiments, the second user device 111 may be a computer, a laptop, a tablet device, a phablet, a server, a mobile device, a smartphone, a smart watch, or any other type of computing device. Illustratively, the second user device 111 is shown as a tablet device in FIG. 1, and the second user 110 is a person.

The system 100 may also include a third user 115, which may be any type of being, such, as but not limited to, a human, an animal, or any other being. The third user 115 may utilize a third user device 116 to also access data, content, and services, and to perform a variety of other functions. For example, the third user device 116 may be utilized by the third user 115 to transmit signals to request various types of content, services, and data provided by providers associated with communications network 135 or any other network in the system 100. Additionally, the third user device 116 may communicate with first and second user devices 102, 111. The third user device 116 may include a memory 117 that includes instructions, and a processor 118 that executes the instructions from the memory 117 to perform the various operations that are performed by the third user device 116. In certain embodiments, the processor 118 may be hardware, software, or a combination thereof. The third user device 116 may also include a camera 119, which may be configured to record and store content within a viewing range of the camera 119. The camera 119 may also record audio content as well. In certain embodiments, the camera 119 may be any type of camera including, but not limited to, a video camera, a photo camera, an infrared camera, a thermal imaging camera, any type of imaging device, or any combination thereof. In certain embodiments, the third user device 116 may be a computer, a laptop, a tablet device, a phablet, a server, a mobile device, a smartphone, a smart watch, or any other type of computing device. Illustratively, the third user device 116 is shown as a tablet device in FIG. 1, and the third user 115 is a physician associated with the first and second users 101, 110.

In certain embodiments, first user device 102, the second user device 111, and the third user device 116 may have any number of software applications and/or application services stored and/or accessible thereon. For example, the first, second, and third user devices 102, 111, 116 may include cloud-based applications, mapping applications, location tracking applications, database applications, gaming applications, internet-based applications, browser applications, mobile applications, service-based applications, productivity applications, video applications, music applications, streaming media applications, social media applications, any other type of applications, any types of application services, or a combination thereof. In certain embodiments, the software applications and services may include one or more graphical user interfaces so as to enable the first, second, and third users 101, 110, 115 to readily interact with the software applications. The software applications and services may also be utilized by the first, second, and third users 101, 110, 115 to interact with the any device in the system 100, any network in the system 100, or any combination thereof. In certain embodiments, the first user device 102, the second user device 111, and the third user device 116 may include associated telephone numbers, device identities, or any other identifiers to uniquely identify the first, second, and third user devices 102, 111, 116.

The system 100 may also include a camera 120, which may be utilized to record any type of media content or any type of other content. The media content may include, but is not limited to, video content, audio content, image content, any type of content, or any combination thereof. The camera 120 may be any type of camera, such as, but not limited to, a video camera, a thermal imaging camera, an infrared camera, an X-ray-enabled camera, any type of imaging device, any type of media content recording device, a surveillance device, or any combination thereof, that may be utilized to capture and record media content associated with the first and second users 101, 110. For example, the camera 120 can record video of the first user 101 and any sounds that the first user 101 makes when the first user 101 is within a viewing range for the camera 120 or the system 100. The camera 120 may record sounds by utilizing a microphone, which may reside within the camera 120 or in proximity to the camera 120. In certain embodiments, the camera 120 may be communicatively linked with any of the devices and networks in the system 100, and may transmit recorded media content to any of the devices and networks in the system 100.

In addition to the camera 120, the system 100 may also include a device 125, which may be any type of device including, but not limited to, an MRI machine, a CT machine, a PET machine, a thermal imaging device, an X-ray machine, an infrared imaging device, any type of medical imaging device, any type of device, any type of computing device, or any combination thereof. In certain embodiments, the device 125 may communicate with any of the devices and components in the system 100, such as, but not limited to, the first, second, and third user devices 102, 111, 116. The device 125 may include a memory 126 that includes instructions, and a processor 127 that executes the instructions from the memory 126 to perform the various operations that are performed by the device 125. In certain embodiments, the processor 127 may be hardware, software, or a combination thereof. The device 125 may be configured to record imaging data and content associated with the first and second users 101, 110. For example, if the device 125 is a thermal imaging device, the device 125 may be configured to take thermal images of the first and second users 101, 110. Using the same example, the thermal images may then be transmitted to any component or device of the system 100 for further processing and may be combined with content obtained from the first, second, and third user devices 102, 111, 116 to assist in detecting anomalies associated with the first and second users 101, 111, and to determine diagnoses for the first and second users 101, 111.

The system 100 may further include a communications network 135. The communications network 135 of the system 100 may be configured to link each of the devices in the system 100 to one another. Additionally, the communications network 135 may be configured to transmit, generate, and receive any information and data traversing the system 100. In certain embodiments, the communications network 135 may include any number of servers, databases, or other componentry. The communications network 135 may also include and be connected to a cloud-computing network, a wireless network, an Ethernet network, a satellite network, a broadband network, a cellular network, a private network, a cable network, the Internet, an internet protocol network, a multiprotocol label switching (MPLS) network, a content distribution network, any network or any combination thereof. Illustratively, servers 140 and 145 are shown as being included within communications network 135, and the communications network 135 is shown as a content delivery network. In certain embodiments, the communications network 135 may be part of a single autonomous system that is located in a particular geographic region, or be part of multiple autonomous systems that span several geographic regions.

Notably, the functionality of the system 100 may be supported and executed by using any combination of the servers 140, 145, and 160. In certain embodiments, the server 140 may include a memory 141 that includes instructions, and a processor 142 that executes the instructions from the memory 141 to perform various operations that are performed by the server 140. The processor 142 may be hardware, software, or a combination thereof. Similarly, the server 145 may include a memory 146 that includes instructions, and a processor 147 that executes the instructions from the memory 146 to perform the various operations that are performed by the server 145. In certain embodiments, the servers 140, 145, and 160 may be network servers, routers, gateways, computers, mobile devices or any other suitable computing device. In certain embodiments, the servers 140, 145 may be communicatively linked to the communications network 135, any network, any device in the system 100, or any combination thereof.

The database 155 of the system 100 may be utilized to store and relay information that traverses the system 100, cache content that traverses the system 100, store data about each of the devices in the system 100 and perform any other typical functions of a database. In certain embodiments, the database 155 may be connected to or reside within the communications network 135, any other network, or a combination thereof. In certain embodiments, the database 155 may serve as a central repository for any information associated with any of the devices and information associated with the system 100. Furthermore, the database 155 may include a processor and memory or be connected to a processor and memory to perform the various operation associated with the database 155. In certain embodiments, the database 155 may be connected to the camera 120, the servers 140, 145, 160, the first user device 102, the second user device 111, the third user device 116, the device 125, the communications network 135, or any combination thereof.

The database 155 may also store information and metadata obtained from the system 100, store metadata and other information associated with the first, second, and third users 101, 110, 115 store user profiles associated with the first, second, and third users 101, 110, 115, store device profiles associated with any device in the system 100, store communications traversing the system 100, store user preferences, store information associated with any device or signal in the system 100, store information relating to patterns of usage relating to the first, second, and third user devices 102, 111, 116, store any information obtained from the communications network 135, or any combination thereof, store any information generated by or associated with the camera 120, store performance data for the devices, store information generated or associated with device 125, store historical data associated with the first and second users 101, 110, store health data associated with the first and second users 101, 110, store information relating to medical conditions, store information associated with anomalies and/or symptoms associated with various medical conditions, store content obtained from the cameras 120 or any device in the system, store any of the information disclosed for any of the operations and functions disclosed herewith, store any information traversing the system 100, or any combination thereof. Furthermore, the database 155 may be configured to process queries sent to it by any device in the system 100.

Operatively, the system 100 may provide video analysis and motion augmentation for applications, such as telemedicine applications, as shown in the following exemplary scenario. In the example scenario, the first user 101 may be located in an office environment and may be utilizing first user device 102, which may be a smartphone or other similar device. The camera 120 of the system 100 may also be located in the office of the first user 101. At a selected time or on a continual basis, the camera 120 may record media content of the first user 101, such as video content of the user, while the first user 101 is sitting in his office. In certain embodiments, the camera 105 may be utilized to record media content associated with the first user 101, either alone or in combination with the camera 120. The media content may be transmitted by the camera 120 to the communications network 135 for further processing. Once the communications network 135 receives the media content, the system 100 may analyze the media content to detect one or more changes associated with the first user 101. For example, the changes may be macro changes and/or micro changes or changes in the condition of the first user 101, or a combination thereof.

Macro changes may be changes or movements specific to the first user's 101 entire body or to a specific region (e.g. chest region, back region, head region, leg region, etc.) of the first user's 101 body. Micro changes may be changes or movements specific to specific body parts and/or to specific body structures (e.g. parts of the face, a single finger, a toe, etc.). For example, the system 100 may detect the first user's 101 blood flow via skin pigmentation changes detected in the media content recorded of the first user 101. As another example, the system 100 may detect various types of range of motion for certain body parts or even detect various types of "ticks" (e.g. eye twitching or restless leg) or habits that the first user 101 has. Changes in movement, for example, may involve detecting that a particular body region is moving in an irregular direction or magnitude. In certain embodiments, the system 100 may be configured to perform a shape analysis (e.g. finding the right rotation or contour of a body part) to help diagnose and normalize automatic observations.

Once the one or more changes associated with the first user 101 are detected based on the media content, the system 100 may detect one or more anomalies associated with the first user 101 based on comparing the detected changes to previously stored information, such as health information, for the first user 101 and/or to aggregated information for a selected population of users. When detecting anomalies, the information obtained from the media content may be combined with images and information obtained from other technologies to confirm the presence of an anomaly. For example, if the first user 101 had an X-ray of his chest and the X-ray shows an anomaly in a certain region, and the media content shows the same anomaly, then the anomaly may be confirmed by utilizing the image provided by the X-ray in conjunction with the video recording of the first user 101. As another example, if the first user 101 underwent a thermal imaging scan using device 125 and the thermal imaging scan showed that the first user's 101 condition is normal, but the media content recording shows an anomaly, the information from the thermal imaging scanning may be utilized to confirm that an anomaly does not exist, and can, therefore, reduce false alarms. In certain embodiments, the first user 101 may be identified by analyzing the media content, and, in other embodiments, the identity of the first user 101 may be kept anonymous. If the first user 101 is identified, the anomaly may be confirmed by comparing the media content recording of the first user 101 to the first user's 101 medical records, which may be accessible by accessing the third user device 116 of the third user 115, who may be a physician.

In certain embodiments, if an anomaly has not been detected or if the existence of an anomaly needs to be confirmed, the system 100 may request that the first user's 101 physician confirm the existence of the anomaly such, as via the third user device 116. Additionally, the system 100 may transmit a signal to automatically adjust a position of the camera 120 or request the user to adjust the position of the first user device 102 so that a new media content recording from a different vantage point may be obtained. Furthermore, the system 100 may transmit a signal to the first user device 102 instructing the user to move a body part or move in a particular manner so that new media content may be recorded to confirm whether an anomaly exists. In certain embodiments, the system 100 may present a visual representation of the first user 101 on a visual interface of the first user device 101 that shows where the detected anomaly is on the first user 101. The system 100 may enable the first user 101 to interact with the visual representation, such as via a software application, to confirm whether the anomaly exists or to input additional information, such as text commentary, associated with the anomaly.

If an anomaly is detected, the system 100 may transmit an alert to the third user device 116 of the physician and/or an alert to the first user device 102 confirming the presence of the anomaly. Based on the detection of the anomaly, the recorded media content, aggregated data for a population and/or historical information for the first user 101, the system 100 may determine one or more proposed interactions for interacting with the first user 101. For example, if the detected anomaly is a bruised wrist, the system 100 may transmit a signal to the third user device 116 requesting the doctor to prescribe medication for dealing with pain associated with the bruised wrist, to input notes relating to the bruised wrist and/or to input a regimen for the first user 101 to perform to heal the bruised wrist. The system 100 may also transmit a signal to the first user device 102 requesting the user to input additional information regarding the cause of the bruising or to input additional information relating to the bruised wrist. In certain embodiments, the signal may advise the first user 101 to adjust a position of the cameras 120, 105 so that further media content may be recorded of the first user 101 so that additional information associated with a detected condition may be obtained. In certain embodiments, the requested interactions may be handled by a health medication service to individually personalize care for the first user 101 and/or to distill the information for a human cooperator. In certain embodiments, the proposed interactions may be adjusted by the physician as necessary.

In certain embodiments, the system 100 may automatically anonymize any of the interactions with the first user 101, the physician, and the system 100. Any information gathered from the interactions may also be anonymized. In certain embodiments, if the identity of the first user 101 is known, confidential information may be scrubbed to ensure the privacy of the first user 101. Additionally, in certain embodiments, based on the severity of the anomaly or condition detected, the system 100 may also automatically scrub information identifying the first user 101 to ensure privacy and confidentiality. The system 100 may generate and transmit any number of interactions to the physician and the first user 101, and may utilize information gathered from the interactions to further supplement the media content and other information obtained for the first user 101.

Based on the information gathered from the interactions, the detected anomaly, the aggregated data, the historical data for the first user 101, or a combination thereof, the system 100 may include determining a diagnosis for the first user 101. For example, using the example above, the system 100 may determine that the first user 101 suffered a specific type of contusion. The determined diagnosis may be provided to the physician and/or confirmed by the physician. If necessary, the determination of the diagnosis may trigger the automatic scheduling of a medical appointment with the physician, such as by accessing digital calendars on the third user device 116 and first user device 102. In certain embodiments, processes provided by the system 100 may be repeated as necessary until enough information associated with the first user 101 is obtained and a confirmation of the diagnosis is possible. The system 100 may also be utilized to complement and support any type of telemedicine applications as well. In certain embodiments, the system 100 may be extended to monitor athlete performance, worker performance, or for any other purpose. Any of the data generated by the system 100 may be stored in a record associated with the first user 101 and may be combined with aggregated data for a population so as to determine various trends in a population and various health conditions for population.

Notably, as shown in FIG. 1, the system 100 may perform any of the operative functions disclosed herein by utilizing the processing capabilities of server 160, the storage capacity of the database 155, or any other component of the system 100 to perform the operative functions disclosed herein. The server 160 may include one or more processors 162 that may be configured to process any of the various functions of the system 100. The processors 162 may be software, hardware, or a combination of hardware and software. Additionally, the server 160 may also include a memory 161, which stores instructions that the processors 162 may execute to perform various operations of the system 100. For example, the server 160 may assist in processing loads handled by the various devices in the system 100, such as, but not limited to, capturing media content of a being; analyzing media content to detect micro and macro movements and changes associated with the being; detecting anomalies based on the media content; transmitting signals to adjust a position of the camera 120, transmitting signals to a device that instruct the being to adjust the being's position; determining proposed interactions with the being; receiving information from the being; determining a diagnosis for the being based on the media content, aggregated data, and other information; and performing any other suitable operations conducted in the system 100 or otherwise. In one embodiment, multiple servers 160 may be utilized to process the functions of the system 100. The server 160 and other devices in the system 100, may utilize the database 155 for storing data about the devices in the system 100 or any other information that is associated with the system 100. In one embodiment, multiple databases 155 may be utilized to store data in the system 100.

Although FIG. 1 illustrates a specific example configuration of the various components of the system 100, the system 100 may include any configuration of the components, which may include using a greater or lesser number of the components. For example, the system 100 is illustratively shown as including a first user device 102, a second user device 111, a third user device 116, a camera 120, a device 125, a communications network 135, a server 140, a server 145, a server 160, and a database 155. However, the system 100 may include multiple first user devices 102, multiple second user devices 111, multiple third user devices 116, multiple cameras 120, multiple devices 125, multiple communications networks 135, multiple servers 140, multiple servers 145, multiple servers 160, multiple databases 155, or any number of any of the other components inside or outside the system 100. Furthermore, in certain embodiments, substantial portions of the functionality and operations of the system 100 may be performed by other networks and systems that may be connected to system 100.

Figure 2:
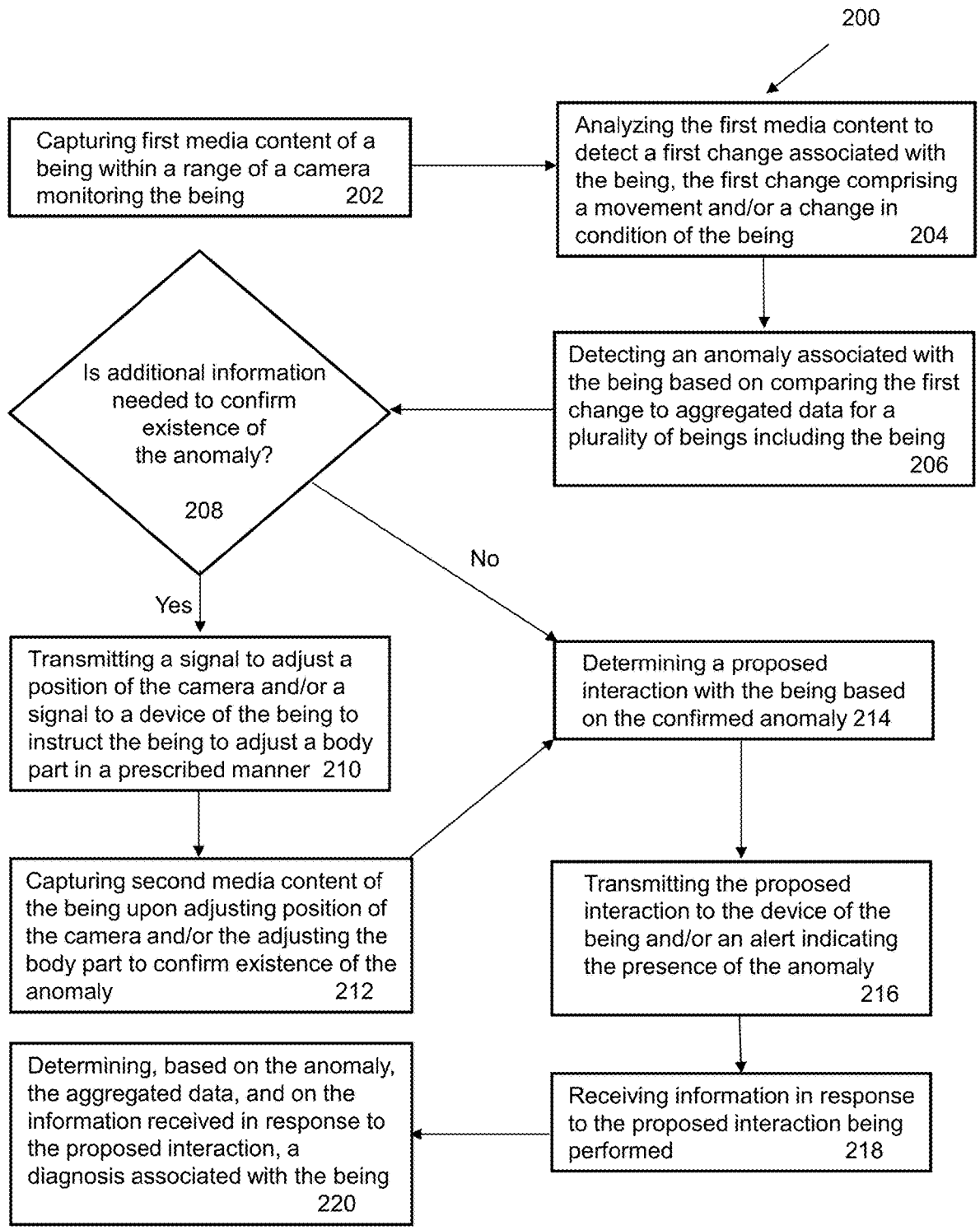
FIG. 2 is a flow diagram illustrating a sample method for providing video analysis and motion augmentation for telemedicine applications according to an embodiment of the present disclosure.

As shown in FIG. 2, an exemplary method 200 for providing video analysis and motion augmentation for applications, such as telemedicine applications, is schematically illustrated. The method 200 may include, at step 202, capturing first media content of a being within a range of a camera 120 monitoring the being. For example, the method 200 may involve utilizing the camera 120 to capture a video recording and/or video stream of the first user 101 at a selected time in a selected environment, such as the first user's 101 office. In certain embodiments, capturing of the media content may be performed by utilizing the first user device 102, the second user device 111, the third user device 116, the camera 120, the device 125, the server 140, the server 145, the server 160, the communications network 135, any combination thereof, or by utilizing any other appropriate program, system, or device.

At step 204, the method 200 may include analyzing the captured media content to detect a first change associated with the being that is monitored. In certain embodiments, the analyzing may be performed by utilizing the first user device 102, the second user device 111, the third user device 116, the camera 120, the device 125, the server 140, the server 145, the server 160, the communications network 135, any combination thereof, or by utilizing any other appropriate program, system, or device. In certain embodiments, the captured media content may be utilized to detect the first change by detecting both micro and macro changes occurring for the being monitored by the camera 120. The micro changes may include changes to a specific body structure of the being, such as, but not limited to, a leg, a hand, a finger, an eye, a mouth, a nose, a thigh, a head, a back, or any other body structure of the being. The macro changes may include changes to the entire body of the being and/or a specific region of the body of the being. The macro and micro changes may be any type of physiological change or even changes that may be symptomatic of certain mental conditions. The physiological changes may include, but are not limited to, any type of body movement, any type of body part movement, any type of skin pigmentation change, any type of skin change, any type of color change, any type of perspiration change, any body fluid change, any type of physiological change, any type of wound, any type of infection, any type of allergic reaction, or any combination thereof. In certain embodiments, textural changes associated with the body of the monitored being may also be detected. For example, a change in texture associated with the being's skin may be detected.

At step 206, the method 200 may include detecting an anomaly associated with the being based on comparing the detected first change with previous historical information for the being, aggregated information for a plurality of other beings, medical information, other information, or a combination thereof. For example, the previous historical information may be obtained from a person's medical records or other records. The historical information may even be inputted by a person into the system 100, such as via a digital form or other input instrument. The aggregated information may be information, such as, but not limited to, health information, demographic information, psychographic information, or any other type of information, for any number of individuals of a selected population. The medical information may include, but is not limited to, information identifying expected health metrics associated with various types of medical conditions, media content displaying healthy body structures, media content displaying unhealthy medical conditions or body structures, healthy and unhealthy human anatomy information, any other types of medical information, or a combination thereof. An anomaly may be detected, for example, if a specific micro-movement of a user's eye that was captured in the media content indicates that the micro-movement is indicative of a degenerative eye disease when the media content is compared with medical information stored in the system 100. The same anomaly may be detected by comparing micro-movement detected in the media content to a person's own medical history, previous media content of the person, or to aggregated data associated with the eyes of a multitude of other people. In certain embodiments, the detecting may be performed by utilizing the first user device 102, the second user device 111, the third user device 116, the camera 120, the device 125, the server 140, the server 145, the server 160, the communications network 135, any combination thereof, or by utilizing any other appropriate program, system, or device.

At step 208, the method 200 may include determining if additional information is needed to confirm the existence of the anomaly. In certain embodiments, the determining may be performed by utilizing the first user device 102, the second user device 111, the third user device 116, the camera 120, the device 125, the server 140, the server 145, the server 160, the communications network 135, any combination thereof, or by utilizing any other appropriate program, system, or device. If it is determined that additional information is needed to confirm the existence of the anomaly, the method 200 may include, at step 210, transmitting a signal to adjust a position of the camera 120 and/or a signal to a device of the being to instruct the being to adjust a body part in a prescribed manner. For example, if the first user 101 is being monitored, a signal may be transmitted by the system 100 to the camera 120 to automatically adjust the camera 120 to a new position so that additional video recordings of the first user 101 may be obtained. As another example, a signal may be transmitted by the system 100 to the first user device 102, which may cause a user interface of the first user device 102 to display instructions to the first user 101 to move his arm up and down in a certain manner.

Once the signal to adjust the position of the camera 120 and/or the signal to the device including instructions is sent, the method 200 may include, at step 212, capturing second media content of the being while the camera 120 position is adjusted, after the camera 120 position is adjusted, while the being adjusts the body part, after the being adjusts the body part, or any combination thereof, to confirm the existence of the anomaly. In certain embodiments, the capturing of the second media content may be performed by utilizing the first user device 102, the second user device 111, the third user device 116, the camera 120, the device 125, the server 140, the server 145, the server 160, the communications network 135, any combination thereof, or by utilizing any other appropriate program, system, or device. Once the second media content is captured or if it is determined that additional information is not needed to confirm the existence of the anomaly, the method 200 may include, at step 214, determining a proposed interaction with the being based on the detection of the anomaly. In certain embodiments, the determining may be performed by utilizing the first user device 102, the second user device 111, the third user device 116, the camera 120, the device 125, the server 140, the server 145, the server 160, the communications network 135, any combination thereof, or by utilizing any other appropriate program, system, or device. A proposed interaction may include, but is not limited to, a request for the being to perform a certain action, a request for a physician to perform some action with respect to the being, a request to change the position of the camera 120 further, a request to have the being take a certain medication, any type of interaction, or any combination thereof.

At step 216, the method 200 may include transmitting the proposed interaction to the device of the being, to a device of a person monitoring the being, or to another device. Also, the method 200 may include transmitting one or more alerts indicating the presence of the anomaly to the being, the person monitoring the being, or a combination thereof. The one or more alerts may also be sent to any device of the system 100. In certain embodiments, the transmitting of the proposed interaction and/or the transmitting of the alerts may be performed by utilizing the server 140, the server 145, the server 160, the communications network 135, any combination thereof, or by utilizing any other appropriate program, system, or device. At step 218, the method 200 may include receiving information in response to the proposed interaction. The information may include, but is not limited to, information associated with an action being performed by the being, information gathered based on an interaction between the being and the person monitoring the being, any information provided in response to the proposed interaction, or any combination thereof. For example, the information may include information provided by a doctor indicating certain additional symptoms associated with the anomaly that doctor has determined to be occurring during the doctor's interaction with the person he is monitoring. In certain embodiments, the information may be received by utilizing the server 140, the server 145, the server 160, the communications network 135, any combination thereof, or by utilizing any other appropriate program, system, or device.

At step 220, the method 200 may include determining, based on the detected anomaly, the aggregated data, the historical information associated with the being, and/or the information received in response to the interaction, a diagnosis for the being. For example, based on the micro-movement of the first user's 101 eye, aggregated data associated with the eyes of multiple other people, previous medical records for the first user 101, and information provided by the doctor relating to the symptoms associated with the micro-movement of the eye, a diagnosis for the first user 101 may be determined. In this case, the system 100 may determine that the first user 101 may have a degenerative eye condition based on the information and media content obtained for the first user 101. The steps in the method 200 may be repeated as necessary until a diagnosis is confirmed and/or until enough information associated with the being and the being's condition is obtained. Notably, the method 200 may further incorporate any of the features and functionality described for the system 100 or as otherwise described herein.

The systems and methods disclosed herein may include additional functionality and features. For example, the systems and methods may be configured to allow for the detection of micro and macro changes associated with a being during selected time intervals. For example, the system 100 may transmit a signal to the camera 120 to record and/or stream video content or other media content of a being for selected time period, such as from 5:00 pm-6:00 pm or a fixed time period of 1 hour. Additionally, the systems and methods may compare micro and macro changes detected during certain time intervals to micro and macro changes detected during other time intervals. Such comparisons may assist in determining whether an anomaly exists and/or whether a certain diagnosis is accurate. In certain embodiments, the cameras 120 may be configured to be placed in any location where a being may be located. For example, one or more cameras 120, 114, 105 may be placed in mass-transit areas, such as, but not limited to, airports, train stations, subways, shopping malls, concerts, theme parks, or any other area. The media content obtained from the cameras 120 may be aggregated and stored in the system 100. The aggregated media content may be utilized to detect pandemics associated with a group of people being monitored, confirm health trends associated with a group of people being monitored, detect anomalies associated with a group of people being monitored, determine diagnoses associated with a group of people being monitored, or a combination thereof. In certain embodiments, media content obtained for a being may be compared to the aggregated media content for a certain population of beings so as to detect the foregoing as well.

The systems and methods may also include detecting anomalies based on a comparison with a corpus of known "normal" or healthy conditions. The corpus may include the monitored being's healthy conditions, a selected population's healthy conditions, or a combination thereof. The anomalies and/or diagnoses may be confirmed based on a comparison against images and outputs generated by other technologies. For example, when evaluated against certain models, probabilistic results, obtained media content, and/or other information generated in the system 100 may be coupled with outputs generated by X-ray machines, CT machines, MRI machines, PET machines, thermal imaging machines, infrared devices, any other technologies, or a combination thereof, to detect anomalies and/or determine diagnoses. The systems and methods may utilize inputs obtained from a traditional medical practitioner's office, such as an office suited with cameras 120, 105, 114, inputs obtained from a self-serve environment (e.g. phone booth with high-rate/resolution cameras 120, 114, 105, a vehicle, or other environment), and/or any number of mobile devices, such as first and second user devices 102, 111. Such inputs may be combined and/or compared with the media content obtained of the being to detect anomalies and/or determine diagnoses.

In certain embodiments, the system 100 may have multiple modes of operation. As a first mode, the system 100 may have an "always on" passive monitoring mode. In such a mode, cameras 120, 105, 114 may monitor any number of beings passively and on a continuous basis. Such a mode may be particularly beneficial in a workplace environment and/or environments that are associated with certain expected injury types. For example, the system 100 may be utilized to monitor office employees to conduct a repetitive stress analysis in an office or to monitor elderly individuals who may benefit from continuous monitoring. During the "always on" mode, information and media content obtained may be aggregated for many people in a feed (e.g. for the public at large or an entire workforce) so as to preempt a pandemic spread of disease or to prevent other conditions from spreading. The system 100 may also have a second mode, which may be an "intentional" scan mode. During "intentional scan" mode, the system 100 may be specifically activated from a sleep state to record and/or stream media content for specific areas and/or beings. The "intentional scan" mode may be particularly beneficial, for example, while a patient visits a doctor at the doctor's office for a medical appointment. The system 100 may further include a "periodic scan" mode, which may involve having the system 100 obtain media content and information for selected areas and beings during periodic time intervals. This may be helpful to determine trends during particular times of the day, to determine when certain conditions occur, or a combination thereof.

In certain embodiments, the systems and methods may include utilizing user feedback when detecting anomalies and/or making diagnoses. The system 100 may transmit a signal to a device of a being, such as the first user device 102 of the first user 101, that requests the being to provide feedback regarding the media content recorded for the being, regarding the being's symptoms, regarding what foods the being ate, regarding any type of information, or any combination thereof. The feedback from the being may be input via a graphical user interface on a device of the being, and may be transmitted to the system 100 for further analysis.

The feedback may be utilized to confirm whether an anomaly exists, adjust a determined diagnosis, confirm an area on the being's body for diagnosis, supplement records associated with the being, supplement detected symptoms for the being, or a combination thereof. System feedback may be utilized to echo symptoms of a region on the being's body that is suspected to be injured and/or infected.

In further embodiments, the systems and methods may include obtaining the media content and information using the cameras 120, 105, 114 after tracers and/or biochemical solutions are either ingested, injected, or otherwise put into the body of a being. For example, a certain tracer may be utilized that is known to trigger an expected response by the body of the being. The cameras 120, 105, 114 may obtain media content of the being while the tracer is coursing through the body of the being, and the media content may be compared to a standard response, which may have been previously imperceptible without micro-change analysis or no longer needs an invasive probe/monitor. The systems and methods may also guarantee that the media content and information obtained for each of the beings is confidential. This may be guaranteed by encrypting the media content and information streams and analyzing the media content and streams in a cloud-computing environment, such as within communications network 135. The systems and methods may allow for a distributed, network-based analysis of video and other media content feeds obtained from a variety of cameras 120, 105, 114 positioned in various areas. In certain embodiments, the media content and information obtained from the cameras 120, 105, 114 may be linked with "big data" collections of diagnoses, which may be particularly helpful in identifying conditions associated with a pandemic before it spreads.

The systems and methods may also institute various triggers based on the media content and information obtained in the system 100. For example, if a certain anomaly and/or diagnosis is detected and/or determined, the systems and methods may automatically transmit alerts or transmit instructions indicating that certain medication should be provided to a particular being. Alerts may also be sent to emergency personnel or even certain government institutions advising of a pandemic, advising of a certain condition, or a combination thereof. In certain embodiments, the systems and methods may include utilizing one or more cameras 120, 105, 114 of different resolutions, capture rates, sampling rates, and capabilities (e.g. storage, lens, processing power, focusing power, pixel dimensions, color capabilities, etc.). For example, a camera 120, 105, 114 that captures media content of a being at one sampling rate may be used to detect certain micro-movements or changes that a camera 120, 105, 114 that has a different sampling rate for capturing media content may not be able to detect. Similarly, media content captured at certain resolutions or by cameras 120, 105, 114 of certain capabilities may be utilized to detect certain macro and micro changes that other media content captured with other cameras 120, 105, 114 or having different resolutions are unable to show. In certain embodiments, the system 100 may adjust the resolutions, capture rates, sampling rates, and capabilities of each individual camera 120, 105, 114 by transmitting one or more signals to each camera 120, 105, 114 indicating what parameters should be adjusted.

In certain embodiments, the cameras 120, 105, 114, the first and second user devices 102, 110, and/or other devices in the system 100 may be utilized to preprocess the media content prior to streaming the media content to the communications network 135 for the detection of anomalies, the determinations of diagnoses, and/or the storage of the media content and information. In certain embodiments, the media content and information obtained from the cameras 120, 105, 114 may be transmitted directly to the components (e.g. edge nodes of the communications network 135) of the system without performing any preprocessing of the media content and information. Once the media content and information are sent to the communications network 135 (e.g. edge nodes) of the system 100 for further analysis, features may be streamed to a model-based comparison system that looks for both local anomalies (e.g. if the being's identity is known and a history for the being is present) or anomalies that are found based on a comparison with information for a general population of beings.

In various embodiments, copies of media content and/or any information in the system 100 that is associated with a being may be anonymized (and personally identifiable, if known) and stored securely in a cloud-based service, such as a service provided by communications network 135. This may ensure that patient privacy is preserved and that the identity of the being is concealed. In certain embodiments, the being may be allowed to interact with the system in a "self-service usage mode." The "self-service usage mode" may utilize additional filtering and distillation of the media content and information associated with the being. The additional filtering and distillation of the media content and information may be utilized to link with ancillary information sources (e.g. patient records, image data provided by MRI machines, CT machines, or other machines, general population data, etc.), connect and schedule medical appointments for the being, schedule follow-up appointments, schedule medical procedures, connect the being with a pharmacy, or any combination thereof.

In further embodiments, the systems and methods may include coupling the system's 100 functionality and operations with information associated with various medications and drugs that induce a response that the functionality and operations of the system 100 may detect. For example, a certain drug may cause a skin reaction, which may be detectable by the cameras 105, 114, 120 of the system 100 and be utilized to detect anomalies, update the monitored being's records, and/or confirm diagnoses. As another example, a trace chemical may cause micro-movements around a bone fracture that may also be detectable by the cameras 105, 114, 120 of the system 100. The systems and methods may be extended to determine anomalies and diagnoses for a large crowd or the public at large to immediately determine health trends, needs, and conditions. The systems and methods may allow for the distributed analysis of medical content in the cloud. Additionally, the systems and methods may be combined with the functionality of a medical robot or electronic doctor that may visit or remotely communicate with a person. On site care may be provided to the person based on the functionality provided by the systems and methods. Furthermore, the functionality and features of the systems and methods may also be combined with robotic surgical devices and may facilitate surgical procedures and the diagnoses of certain medical conditions.

Figure 3:
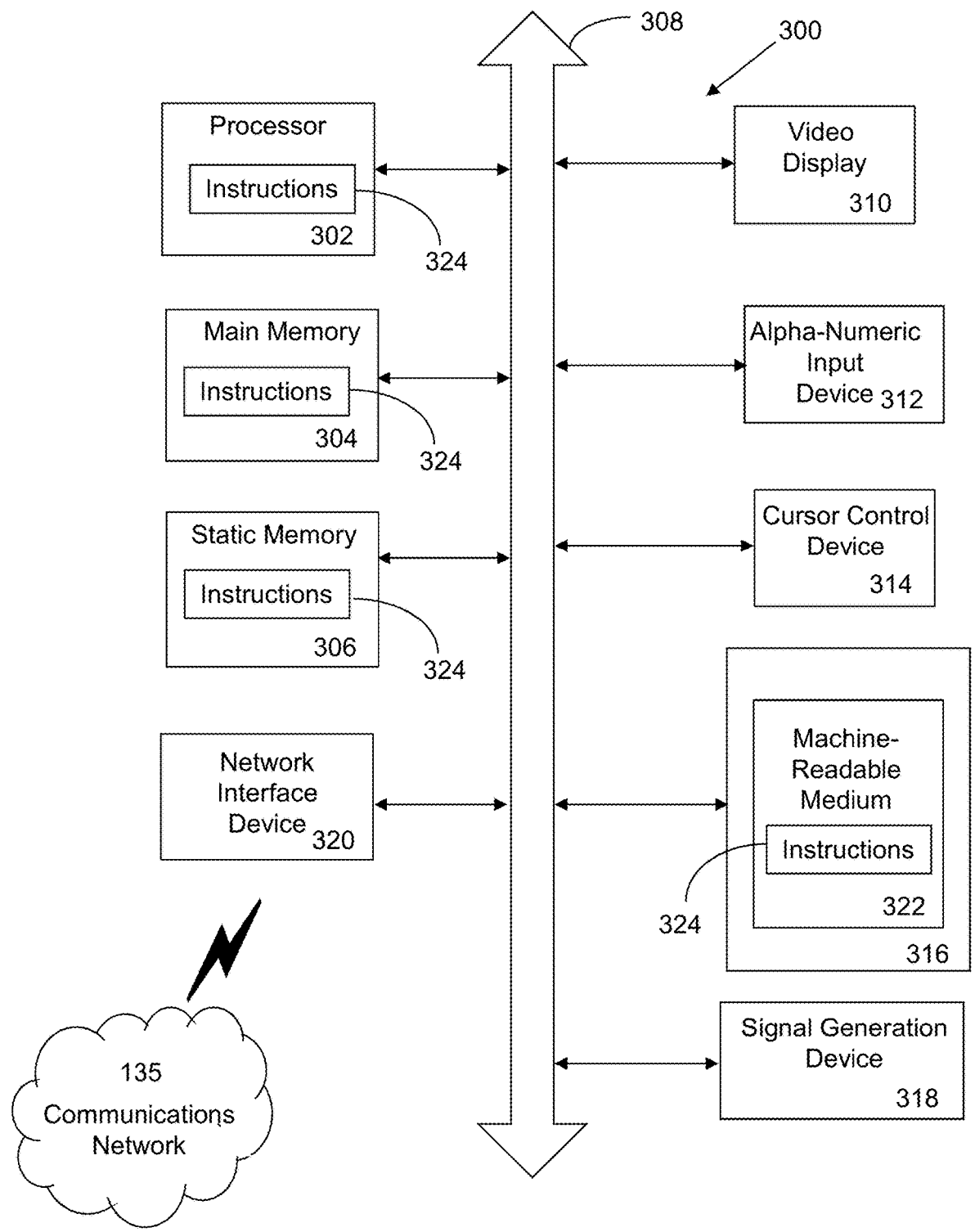
FIG. 3 is a schematic diagram of a machine in the form of a computer system within which a set of instructions, when executed, may cause the machine to perform any one or more of the methodologies or operations of the systems and methods for providing video analysis and motion augmentation for telemedicine applications.

Referring now also to FIG. 3, at least a portion of the methodologies and techniques described with respect to the exemplary embodiments of the system 100 can incorporate a machine, such as, but not limited to, computer system 300, or other computing device within which a set of instructions, when executed, may cause the machine to perform any one or more of the methodologies or functions discussed above. The machine may be configured to facilitate various operations conducted by the system 100. For example, the machine may be configured to, but is not limited to, assist the system 100 by providing processing power to assist with processing loads experienced in the system 100, by providing storage capacity for storing instructions or data traversing the system 100, or by assisting with any other operations conducted by or within the system 100.

In some embodiments, the machine may operate as a standalone device. In some embodiments, the machine may be connected (e.g., using communications network 135, another network, or a combination thereof) to and assist with operations performed by other machines and systems, such as, but not limited to, the first user device 102, the second user device 111, the third user device 116, the camera 120, the device 125, the server 140, the server 145, the database 155, the server 160, or any combination thereof. The machine may be connected with any component in the system 100. In a networked deployment, the machine may operate in the capacity of a server or a client user machine in a server-client user network environment, or as a peer machine in a peer-to-peer (or distributed) network environment. The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The computer system 300 may include a processor 302 (e.g., a central processing unit (CPU), a graphics processing unit (GPU, or both), a main memory 304 and a static memory 306, which communicate with each other via a bus 308. The computer system 300 may further include a video display unit 310, which may be, but is not limited to, a liquid crystal display (LCD), a flat panel, a solid state display, or a cathode ray tube (CRT). The computer system 300 may include an input device 312, such as, but not limited to, a keyboard, a cursor control device 314, such as, but not limited to, a mouse, a disk drive unit 316, a signal generation device 318, such as, but not limited to, a speaker or remote control, and a network interface device 320.

The disk drive unit 316 may include a machine-readable medium 322 on which is stored one or more sets of instructions 324, such as, but not limited to, software embodying any one or more of the methodologies or functions described herein, including those methods illustrated above. The instructions 324 may also reside, completely or at least partially, within the main memory 304, the static memory 306, or within the processor 302, or a combination thereof, during execution thereof by the computer system 300. The main memory 304 and the processor 302 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a computer processor. Furthermore, software implementations can include, but not limited to, distributed processing or component/object distributed processing, parallel processing, or virtual machine processing can also be constructed to implement the methods described herein.

The present disclosure contemplates a machine-readable medium 322 containing instructions 324 so that a device connected to the communications network 135, another network, or a combination thereof, can send or receive voice, video or data, and communicate over the communications network 135, another network, or a combination thereof, using the instructions. The instructions 324 may further be transmitted or received over the communications network 135, another network, or a combination thereof, via the network interface device 320.

While the machine-readable medium 322 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that causes the machine to perform any one or more of the methodologies of the present disclosure.

The terms "machine-readable medium," "machine-readable device," or "computer-readable device" shall accordingly be taken to include, but not be limited to: memory devices, solid-state memories such as a memory card or other package that houses one or more read-only (non-volatile) memories, random access memories, or other re-writable (volatile) memories; magneto-optical or optical medium such as a disk or tape; or other self-contained information archive or set of archives is considered a distribution medium equivalent to a tangible storage medium. The "machine-readable medium," "machine-readable device," or "computer-readable device" may be non-transitory, and, in certain embodiments, may not include a wave or signal per se. Accordingly, the disclosure is considered to include any one or more of a machine-readable medium or a distribution medium, as listed herein and including art-recognized equivalents and successor media, in which the software implementations herein are stored.

The illustrations of arrangements described herein are intended to provide a general understanding of the structure of various embodiments, and they are not intended to serve as a complete description of all the elements and features of apparatus and systems that might make use of the structures described herein. Other arrangements may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific arrangements have been illustrated and described herein, it should be appreciated that any arrangement calculated to achieve the same purpose may be substituted for the specific arrangement shown. This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The foregoing is provided for purposes of illustrating, explaining, and describing embodiments of this invention. Modifications and adaptations to these embodiments will be apparent to those skilled in the art and may be made without departing from the scope or spirit of this invention. Upon reviewing the aforementioned embodiments, it would be evident to an artisan with ordinary skill in the art that said embodiments can be modified, reduced, or enhanced without departing from the scope and spirit of the claims described below.

We claim:

1. A system, comprising:
    a memory that stores instructions; and
    a processor that executes the instructions to perform operations, the operations comprising:
        capturing first media content of a being within a range of a first camera monitoring the being;
        analyzing the first media content to detect a first change associated with the being, wherein the first change associated with the being comprises a first movement of the being, a first change in a condition of the being, or a combination thereof;
        detecting an anomaly associated with the being based on comparing the first change associated with the being to aggregated data for a plurality of beings including the being;
        determining, based on the anomaly associated with the being, a proposed interaction with the being;
        transmitting the proposed interaction to a device of the being;
        determining, based on the anomaly, the aggregated data, and on information obtained in response to transmitting the proposed interaction, a diagnosis associated with the being; and
        confirming the diagnosis based on other media content captured by a second camera that has a first sampling rate that is different from a second sampling rate of the first camera, wherein the second camera having the first sampling rate is configured to capture different motion than the first camera having the second sampling rate, wherein the different motion captured by the second camera includes a second movement of the being that the first camera is unable to detect.

2. The system of claim 1, wherein the operations further comprise transmitting a signal to adjust a position of the first camera to capture second media content of the being, wherein the signal is transmitted with the proposed interaction.

3. The system of claim 2, wherein the operations further comprise analyzing the second media content to detect a second change associated with the being, and wherein the operations further comprise adjusting the diagnosis based on analysis of the first change, the second change, the aggregated data, and the anomaly.

4. The system of claim 1, wherein the operations further comprise detecting the first change associated with the being based on analyzing the first media content in combination with infrared imaging content of the being, thermal imaging content of the being, or a combination thereof.

5. The system of claim 1, wherein the operations further comprise anonymizing data associated with the being, wherein the data associated with the being comprises the anomaly, the first media content, and the diagnosis.

6. The system of claim 1, wherein the operations further generating an alert after detecting the anomaly.

7. The system of claim 1, wherein the operations further comprise transmitting a signal instructing the being to adjust a body part after detecting an anomaly associated with the being, wherein the signal is transmitted to the device of the being.

8. The system of claim 7, wherein the operations further comprise capturing second media content of the being after the being adjusts the body part in response to the signal.

9. The system of claim 8, wherein the operations further comprise confirming whether the anomaly exists based on analyzing the second media content of the being.

10. The system of claim 9, wherein the operations further comprise adjusting the diagnosis associated with the being if the anomaly is not confirmed to exist.

11. The system of claim 1, wherein the operations further comprise adjusting a sampling rate associated with capturing the first media content to correspond with a type of the first change to be detected.

12. A method, comprising:
    obtaining, during a first time interval, first media content of a being within a range of a first camera monitoring the being;
    detecting, based on the first media content, a first change associated with the being, wherein the first change associated with the being comprises a first movement of the being, a first change in a condition of the being, or a combination thereof;
    detecting, by utilizing instructions from a memory that are executed by a processor, an anomaly associated with the being based on comparing the first change associated with the being to aggregated data for a plurality of beings;
    determining, based on the anomaly associated with the being, a proposed interaction with the being;
    transmitting the proposed interaction to a device associated with the being;
    determining, based on the anomaly, the aggregated data, and on information obtained in response to transmitting the proposed interaction, a diagnosis associated with the being; and
    confirming the diagnosis based on other media content captured by a second camera that has a first sampling rate that is different from a second sampling rate of the first camera, wherein the second camera having the first sampling rate is configured to capture different motion than the first camera having the second sampling rate, wherein the different motion captured by the second camera includes a second movement of the being that the first camera is unable to detect.

13. The method of claim 12, further comprising obtaining, during a second time interval, second media content of the being within the range of the first camera monitoring the being.

14. The method of claim 13, further comprising comparing the first media content with the second media content to confirm whether the anomaly exists.

15. The method of claim 12, further comprising transmitting a signal to adjust a position of the first camera to capture second media content of the being, wherein the signal is transmitted with the proposed interaction.

16. The method of claim 15, further comprising analyzing the second media content to detect a second change associated with the being, and wherein the operations further comprise adjusting the diagnosis based on analysis of the second change.

17. The method of claim 12, further comprising identifying the being based on the first media content.

18. The method of claim 12, further comprising anonymizing data associated with the being if a severity of the diagnosis exceeds a threshold.

19. The method of claim 12, further comprising entering into an always-on mode, and further comprising capturing additional media content for the plurality of beings during the always-on mode.

20. A non-transitory computer-readable device comprising instructions, which when executed by a processor, cause the processor to perform operations comprising:

capturing first media content of a being within a range of a first camera;

analyzing the first media content to detect a first change associated with the being, wherein the first change associated with the being comprises a first movement of the being, a first change in a condition of the being, or a combination thereof;

detecting an anomaly associated with the being based on comparing the first change associated with the being to aggregated data for a plurality of beings;

determining, based on the anomaly associated with the being, a proposed interaction with the being to determine a diagnosis associated with the being;

transmitting the proposed interaction to a device associated with the being;

determining, based on the anomaly, the aggregated data, and on information obtained in response to transmitting the proposed interaction, the diagnosis associated with the being; and confirming the diagnosis based on other media content captured by a second camera that has a first sampling rate that is different from a second sampling rate of the first camera, wherein the second camera having the first sampling rate is configured to capture different motion than the first camera having the second sampling rate, wherein the different motion captured by the second camera includes a second movement of the being that the first camera is unable to detect.

* * * * *